(12) United States Patent
Mossler et al.

(10) Patent No.: US 8,338,378 B2
(45) Date of Patent: Dec. 25, 2012

(54) NEUROTROPHIC PEPTIDES

(75) Inventors: Herbert Mossler, Seekirchen (AT); Khalid Iqbal, Staten Island, NY (US); Inge Grundke-Iqbal, Staten Island, NY (US)

(73) Assignee: Research Foundation For Mental Hygiene, Inc., Menands, NY (US)

( * ) Notice: Subject to any disclaimer, the term of this patent is extended or adjusted under 35 U.S.C. 154(b) by 27 days.

(21) Appl. No.: 12/531,616

(22) PCT Filed: Mar. 17, 2008

(86) PCT No.: PCT/EP2008/002106
§ 371 (c)(1),
(2), (4) Date: Sep. 16, 2009

(87) PCT Pub. No.: WO2008/113536
PCT Pub. Date: Sep. 25, 2008

(65) Prior Publication Data
US 2010/0029572 A1 Feb. 4, 2010

(30) Foreign Application Priority Data
Mar. 16, 2007 (EP) .................................... 07450050

(51) Int. Cl.
*A01N 37/18* (2006.01)
*A61K 38/04* (2006.01)

(52) U.S. Cl. ..................... 514/17.7; 514/16.5; 514/18.2; 530/327; 530/328; 530/330

(58) Field of Classification Search .................. None
See application file for complete search history.

(56) References Cited

U.S. PATENT DOCUMENTS

| 3,846,399 | A | 11/1974 | Hirschmann et al. ......... 530/342 |
| 6,472,178 | B1 * | 10/2002 | Fandl et al. .................. 435/69.4 |
| 7,304,129 | B2 | 12/2007 | Saffell ........................ 530/328 |
| 2004/0102370 | A1 | 5/2004 | Saffell ........................... 514/12 |

FOREIGN PATENT DOCUMENTS

| WO | WO 91/04316 | 4/1991 |
| WO | WO 94/25482 | 11/1994 |
| WO | WO 99/43813 | 9/1999 |
| WO | WO 02/070698 | 9/2002 |
| WO | WO 2004/016653 | 2/2004 |
| WO | WO 2004/063963 | 7/2004 |
| WO | WO 2005/010043 | 2/2005 |
| WO | WO 2005/033137 | 4/2005 |
| WO | WO 2006/081249 | 8/2006 |

OTHER PUBLICATIONS

He et al., "Preparation and a structure-function analysis of human ciliary neurotrophic factor," *Neurosci. Res.*, 23:327-33, 1995.
Hughes et al., "Ciliary neurotrophic factor induces type-2 astrocyte differentiation in culture," *Nature*, 335:70-3, 1988.
International Search Report issued in Application No. PCT/EP2008/002106, date of mailing Mar. 9, 2008.
Krüttgen et al., "Human ciliary neurotrophic factor: a structure-function analysis," *Biochem. J.*, 309:215-20, 1995.
Masiakowski et al., "Recombinant human and rat ciliary neurotrophic factors," *J Neurochem.*, 57:1003-1012, 1991.
Negro et al., "Structure-function studies of human ciliary neurotrophic factor," *Neurochem. Res.*, 19:223-227, 1994.
Panayotatos et al., "Localization of functional receptor epitopes on the structure of ciliary neurotrophic factor indicates a conserved, function-related epitope topography among helical cytokines," *J. Biol. Chem.*, 270:14007-14, 1995.
Sendtner et al., "Ciliary neurotrophic factor prevents the degeneration of motor neurons after axotomy," *Nature*, 345:440-1, 1990.
Skaper and Varon, "Age-dependent control of dorsal root ganglion neuron survival by macromolecular and low-molecular-weight trophic agents and substratum-bound laminins," *Brain Res.*, 389:39-46, 1986.

* cited by examiner

*Primary Examiner* — Olga N Chernyshev
(74) *Attorney, Agent, or Firm* — David L. Nocilly; Bond Schoeneck & King, PLLC

(57) ABSTRACT

The present invention relates to a neurotrophic peptide having an amino acid sequence selected from the group consisting of VGDGGLFEKKL (SEQ ID NO: 1), EDQQVHFTPTEG (SEQ ID NO: 2) and IPENEADGMPATV (SEQ ID NO: 3).

16 Claims, 7 Drawing Sheets

Red: BrdU-IR cells
Green: DCX-IR cells (a)

(b)

(c)

(a)

(b)

(a)

(b)

(a)

(b)

(c)

NEUROTROPHIC PEPTIDES

This application is a national phase application under 35 U.S.C. §371 of International Application No. PCT/EP2008/002106 filed 17 Mar. 2008, which claims priority to European Application No. 07450050.5 filed 16 Mar. 2007. The entire text of each of the above-referenced disclosures is specifically incorporated herein by reference without disclaimer.

The present invention relates to neurotrophic and/or neurogenic peptides and their use for manufacturing a medicament for the treatment of neurodegenerative diseases.

The population in the industrialised countries is rapidly ageing due to a greater life expectancy, and an ever-increasing number of people are afflicted with neurodegenerative diseases making a global issue out of these diseases.

Neurodegenerative diseases result from the gradual and progressive loss of neural cells, leading to nervous system dysfunction, and may have next to ageing various causes (e.g. environmental influences, genetic defects). Till now more than 600 neurologic disorders are known.

The major known risk factors for neurodegenerative disease include certain genetic polymorphisms and increasing age. Other possible causes may include gender, poor education, endocrine conditions, oxidative stress, inflammation, stroke, hypertension, diabetes, smoking, head trauma, depression, infection, tumors, vitamin deficiencies, immune and metabolic conditions, and chemical exposure. Because the pathogenesis of many of these diseases remains unknown, also the role of environmental factors in these diseases may be considered. An overview of neurodegenerative diseases can be found, for instance, in "Neurodegenerative Diseases: Neurobiology, Pathogenesis and Therapeutics" (M. Flint Beal, Anthony E. Lang, and Albert C. Ludolph; Cambridge University Press; 2005).

In order to treat neurodegenerative diseases several medicaments comprising one or more active compounds like Piracetam, Nimotop, Vinpocetin, Gliatilin, Cerebrolysin, Cytoflavin etc. are regularly employed. The compounds known in the art have varying modes of action. Cerebrolysin, for instance, a peptide based drug produced from purified animal brain proteins by standardized enzymatic breakdown, is exerting nerve growth factor like activity on neurons from dorsal root ganglia, neurotrophic and neuroprotective effects.

US 2004/102370 relates to peptides comprising the essential tetrameric peptide structural unit Xaa-Xaa-Xaa-Xaa in which Xaa at position 1 represents Glu or Asp, Xaa at position 2 represents any amino acid, Xaa at position 3 represents any amino acid and Xaa at position 4 represents Glu or Asp. Said peptides are used to treat neurodegenerative diseases and nerve damages, and are described to be stimulators of axonal regeneration and survival.

Ciliary neurotrophic factor (CNTF) is a survival factor for various neuronal cell types. The human CNTF protein comprises 200 amino acid residues and shares significant sequence homology with CNTF proteins from other mammalian sources. The gene for human CNTF has been cloned and recombinant forms of the protein are available for clinical trials in humans (WO 91/04316). Over the past decade, a number of biological effects have been ascribed to CNTF in addition to its ability to support the survival of ciliary ganglion neurons. CNTF is believed to induce the differentiation of bipotential glial progenitor cells in the perinatal rat optic nerve and brain (Hughes et al., 1988, Nature 335:70-73). Furthermore, it has been observed to promote the survival of embryonic chick dorsal root ganglion sensory neurons (Skaper and Varon, 1986, Brain Res. 389:39-46). In addition, CNTF supports the survival and differentiation of motor neurons, hippocampal neurons and presympathetic spinal cord neurons (Sendtner, et al., 1990, Nature 345: 440-441).

In addition to human CNTF, the corresponding rat and rabbit genes have been cloned and found to encode a protein of 200 amino acids, which share about 80% sequence identity with the human gene.

Despite their structural and functional similarity, recombinant human and rat CNTF differ in several respects. The biological activity of recombinant rat CNTF in supporting survival and neurite outgrowth from embryonic chick ciliary neurons in culture is four times better than that of recombinant human CNTF (Masiakowski et al., 1991, J. Neurochem. 57:1003-1012). Further, rat CNTF has a higher affinity for the human CNTF receptor than does human CNTF.

As described in WO 99/43813 one of the uses of CNTF is the use of CNTF for the treatment of Huntington's disease. Huntington's disease (HD) is an hereditary degenerative disorder of the central nervous system.

However, the administration of CNTF to the human body has several drawbacks. While its therapeutic potential for CNS diseases is well recognized, the blood brain barrier (BBB) hinders the systemic delivery of CNTF and direct bolus injections are not suitable due to the short half-life of CNTF. One method of overcoming the blood brain barrier while providing continuous delivery of CNTF is, e.g., with immunoisolated cellular implants that produce and deliver CNTF directly to the region of interest. Cells can be protected from host rejection by encapsulating, or surrounding, them within an immunoisolatory, semipermeable membrane that admits oxygen and required nutrients and releases bioactive cell secretions, but restricts passage of larger cytotoxic agents from the host immune defense system. The selective membrane eliminates the need for chronic immunosuppression of the host and allows the implanted cells to be obtained from nonhuman sources. However, also this method is not advantageous.

It is an object of the present invention to provide new medicaments comprising substances which have substantially the same or even better neurotrophic and/or neurogenic effects than CNTF. Advantageously these substances should also be able to pass the blood brain barrier in order to reach the wanted site of action in the brain.

Therefore, the present invention relates to a neurotrophic and/or neurogenic peptide having an amino acid sequence selected from the group consisting of VGDGGLFEKKL (SEQ ID NO: 1), EDQQVHFTPTEG (SEQ ID NO: 2) or IPENEADGMPATV (SEQ ID NO: 3).

It has surprisingly been found that the peptides of the present invention, which are derivable from rat or human CNTF, show neurotrophic and/or neurogenic (causing growth of nerve tissue) effects which are comparable to the wild-type CNTF. Furthermore due to their small size these peptides are also able to pass the blood brain barrier.

Fragments of SEQ ID No. 1 to 3 preferably comprise 4 to 10, more preferably 4 to 8, even more preferably 4 to 6, amino acids and include:

| Source | Sequence | SEQ ID NO: |
|---|---|---|
| SEQ ID NO: 1 | GDGGLFEK | 5 |
| | GLFEKKLW | 6 |
| | VGDG | 7 |
| | GDGG | 8 |

-continued

| Source | Sequence | SEQ ID NO: |
|---|---|---|
| | DGGL | 9 |
| | GGLF | 10 |

The peptides of the present invention and their fragments may be fused to other proteins, polypeptides or peptides (N- or C-terminally), or conjugated to other substances. The resulting fusions may also comprise more than one peptide of the present invention (e.g. SEQ ID NO: 1 may be fused to SEQ ID NO: 2). The peptides of these polypeptides may be fused directly or via a linker to each other. Therefore, the present invention also relates to a polypeptide comprising at least two, preferably at least three, peptides of the present invention (SEQ ID NOs: 1 to 10).

The peptides of the present invention may also be bound or conjugated to substances which enhance their ability to pass through the blood brain barrier.

"Fragments", as used herein, refer to parts of the peptides of the present invention, which are directly derivable from said peptides and show the same as or enhanced neurotrophic and neurogenic activities than the wild-type CNTF.

According to the present invention also peptides are encompassed which exhibit at least 80%, preferably 90%, more preferably 95%, identity with the peptides of the present invention selected from the group consisting of SEQ ID NOs: 1 to 3.

According to the present invention "identity" ("identical") is determined by comparing two optimally aligned sequences over a comparison window, where the fragment of the amino acid sequence in the comparison window may comprise additions or deletions (e.g., gaps or overhangs) as compared to the reference sequence (which does not comprise additions or deletions) for optimal alignment of the two sequences. In general, sequences are aligned so that the highest order match is obtained (see, e.g.: Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; Carillo et al. (1988) SIAM J Applied Math 48:1073).

Whether any two amino acid molecules have amino sequences that are at least, for example, 80%, 85%, 90%, 95%, 96%, 97%, 98% or 99% "identical", can be determined using known computer algorithms such as the "FAST A" program, using for example, the default parameters as in Pearson et al. (1988) PNAS USA 85: 2444 (other programs include the GCG program package (Devereux, J., et al., Nucleic Acids Research (1984) Nucleic Acids Res., 12, 387-395), BLASTP, BLASTN, FASTA (Atschul, S. F., et al., J Molec Biol 215: 403 (1990); Guide to Huge Computers, Martin J. Bishop, ed., Academic Press, San Diego, 1994, and Carillo et al, (1988) SIAM J Applied Math 48: 1073). For instance, the BLAST tool of the NCBI database can be used to determine identity. Other commercially or publicly available programs include, DNAStar "MegAlign" program (Madison, Wis.) and the University of Wisconsin Genetics Computer Group (UWG) "Gap" program (Madison Wu)). Percent identity of proteins and/or peptides can be determined, for example, by comparing sequence information using a GAP computer program (e.g. Needleman et al., (1970) J. Mol. Biol. 48:443, as revised by Smith and Waterman (1981) Adv. Appl. Math. 2:482). Briefly, the GAP program defines similarity as the number of aligned symbols (i.e., nucleotides or amino acids) which are similar, divided by the total number of symbols in the shorter of the two sequences. Default parameters for the GAP program can include: (1) a unary comparison matrix (containing a value of 1 for identities and for non-identities) and the weighted comparison matrix of Gribskov et al. 14:6745, as described by Schwartz and Dayhoff, eds., ATLAS OF PROTEIN SEQUENCE AND STRUCTURE, National Biomedical Research Foundation, pp. 353-358 (1979); (2) a penalty of 3.0 for each gap and an additional 0.10 penalty for each symbol in each gap; and (3) no penalty for end gaps.

As used herein, the term "at least 80% identical to" refers to percent identities from 80 to 99.99 relative to the reference peptides. Consequently, the peptides of the present invention may also comprise one or more amino acid modifications (i.e. substitutions, deletions, insertions) provided that the peptides still exhibit neurotrophic and/or neurogenic activity.

Identity at a level of 80% or more is indicative of the fact that, assuming for exemplification purposes a test and reference polypeptide length of 100 amino acids is compared, no more than 20% (i.e. 20 out of 100) of amino acid residues in the test polypeptide differs from that of the reference polypeptide. Such differences can be represented as point mutations randomly distributed over the entire length of an amino acid sequence or they can be clustered in one or more locations of varying length up to the maximum allowable, e.g. 20/100 amino acid difference (approx. 80% identity). Differences are defined as amino acid substitutions, insertions or deletions. At the level of homologies or identities above about 85-90%, the result should be independent of the program and gap parameters set; such high levels of identity can be assessed readily, often without relying on software.

According to a preferred embodiment of the present invention the neurotrophic peptide of the present invention is identical to SEQ ID NOs: 1, 2 or 3, which means that the neurotrophic peptide consists of said amino acids sequences or fragments thereof. Of course, the peptide of the present invention may comprise modifications such as substitution of L-amino acids with D-amino acids, introduction of hydrophobic side chains, modifications allowing the formation of dimers (or even multimers) or cyclic peptide variants. The respective methods are well known in the art.

The peptide according to the present invention is preferably non immunogenic. The term "non immunogenic peptide" as used herein refers to a molecule, in particular to a peptide, which does substantially not provoke an immune response in vivo when administered to a human or an animal being. This molecule property can be determined by methods known in the art. For instance, if the administration of a molecule according to the present invention to an animal (e.g. rabbit, mouse) provokes in an animal a substantial increase of antibodies directed against said molecule, said molecule is considered as an "immunogenic peptide", if, however, substantially no molecule-specific anti-bodies can be induced in an animal or human upon administration of said molecule, it is considered as a "non immunogenic peptide". It is important that the peptides according to the present invention are non immunogenic because immunogenic peptides are normally eliminated from the body by the immune system.

The basic structure of the peptide according to the present invention, which is formed by amino acids, is preferably synthesised chemically according to methods known in the art, e.g. by the method developed by Merrifield et al. (Merrifield, R. B. (1963) J. Am. Chem. Soc. 85, 2149-2154; solid phase peptide synthesis).

The solid phase peptide synthesis method introduced by Merrifield in 1963, for instance, involves the attachment of a growing peptide chain to a solid support. An amino acid corresponding to the C-terminal of the target peptide is covalently attached to an insoluble polymeric support (the "resin"). The next amino acid, with a protected alpha-amino acid, is activated and reacted with the resin-bound amino acid to yield an amino-protected dipeptide on the resin. The amino-protecting group is removed and chain extension is continued with the third and subsequent protected amino acids. After the target protected peptide chain has been built up the resin is cleaved by suitable chemical means thereby releasing the crude peptide product into solution (for solid phase peptide synthesis methods and other peptide synthesis methods see also Fields, G. B. (ed.), *Solid-Phase Peptide Synthesis in Methods in ENZYMOLOGY*, Vol. 289, Academic Press, San Diego (1997); Bodansky, M., Bodansky, A., The practice of peptide synthesis (2nd edn.), Springer Verlag, Berlin (1995); Pennington, M. W., Dunn, B. M. (eds), Peptide Synthesis Protocols, in Methods in Molecular Biology, Vol. 35, Humana Press Inc., Totowa (1994); Grant, G. A. (ed.), Synthetic peptides: a user's guide, W.H. Freemann & Co., New York (1992)).

The inorganic cation at the C-terminal end of the peptide according to the present invention may be an alkali metal or alkali earth metal cation, preferably a lithium, sodium, potassium, magnesium or calcium cation.

These inorganic cations are regularly used to prepare salts of pharmaceutically active substances.

The organic cation may be a quaternary ammonium ion.

If the N-terminal end of the peptide according to the present invention comprises a positive charge, said charge may be preferably compensated by an equivalent of an inorganic or organic anion. The organic anion can be, for instance, acetate anion.

Of course it is also possible to use molecules, preferably small molecules, mimicking the peptides of the present invention.

Another aspect of the present invention relates to a pharmaceutical composition comprising at least one peptide according to the present invention and/or at least one peptide having an amino acid sequence selected from the group consisting of GDGGLFEK (SEQ ID NO: 5), GLFEKKLW (SEQ ID NO: 6), VGDG (SEQ ID NO: 7), GDGG (SEQ ID NO: 8), DGGL (SEQ ID NO: 9) and GGLF (SEQ ID NO: 10) and optionally at least one pharmaceutically acceptable excipient and/or carrier.

The peptide according to the present invention may be formulated in a pharmaceutical preparation, which can be administered to a patient for preventing or treating a cerebral disease, in particular a neurodegenerative disease. The pharmaceutical preparation may further comprise pharmaceutically acceptable excipients and/or carriers. Suitable excipients and carriers are well known in the art (see e.g. "Handbook of Pharmaceutical Excipients", 5th Edition by Raymond C. Rowe, Paul J. Sheskey, Siân C. Owen (2005), APhA Publications).

The composition of the present invention may further comprise at least one additional pharmaceutically active component, which is preferably IPRNEADGMPINV (SEQ ID NO: 4).

The pharmaceutical preparation according to the present invention may comprise next to the peptide according to the present invention further active components, which may exhibit similar properties when administered to an individual or which may cause other reactions in the treated patient.

According to the present invention, e.g., antioxidants like vitamins may be considered as further active components because antioxidants inhibit oxidation or suppress reactions promoted by oxygen, oxygen free radicals, oxygen reactive species including peroxides. Antioxidants, especially lipid-soluble antioxidants, can be absorbed into the cell membrane to neutralize oxygen radicals and thereby protect the membrane. The antioxidants useful in the present invention are preferably vitamin antioxidants that may be selected from the group consisting of all forms of Vitamin A including retinal and 3,4-didehydroretinal, all forms of carotene such as alpha-carotene, beta-carotene, gamma-carotene, delta-carotene, all forms of Vitamin C (D-ascorbic acid, L-ascorbic acid), all forms of tocopherol such as Vitamin E (Alpha-tocopherol, 3,4-dihydro-2,5,7,8-tetramethyl-2-(4,8,12-trimethyltri-decyl)-2H-1-benzopyran-6-ol), beta-tocopherol, gamma-tocopherol, delta-tocopherol, tocoquinone, tocotrienol and Vitamin E esters which readily undergo hydrolysis to Vitamin E such as Vitamin E acetate and Vitamin E succinate, and pharmaceutically acceptable Vitamin E salts such as Vitamin E phosphate, prodrugs of Vitamin A, carotene, Vitamin C, and Vitamin E, pharmaceutically acceptable salts of Vitamin A, carotene, Vitamin C, and Vitamin E, and the like, and mixtures thereof.

According to another preferred embodiment of the present invention the composition is provided for intravenous, intramuscular, spinal, epidural, transdermal, intranasal, mucosal, parenteral, oral, enteral or rectal administration.

Depending on the route of administration the pharmaceutical composition according to the present invention may be formulated, for instance, as tablets, capsules, liquids, infusion and suppositories (see e.g. "Pharmaceutical Formulation Development of Compounds" by Sven Frokjaer (1999), CRC; "Handbook of Pharmaceutical Manufacturing Formulations" by Sarfaraz K. Niazi (2004), CRC).

The peptides are preferably comprised in the composition in an amount between 0.1 µg/g to 100 mg/g, preferably 1 µg/g to 80 mg/g. In any way, the effective dosages for prevention or treatment of human patients can be optimised for given patients or patient collectives according to the routine methods available for the present field.

Another aspect of the present invention relates to the use of at least one peptide with neurotrophic and/or neurogenic activity as defined above which may be part of a molecule consisting of a maximum of 50, preferably a maximum of 40, more preferred a maximum of 30, even more preferred a maximum of 20, amino acids, and/or at least one peptide having an amino acid sequence selected from the group consisting of G-D-G-G-L-F-E-K (SEQ ID NO: 5), G-L-F-E-K-K-L-W (SEQ ID NO: 6), V-G-D-G (SEQ ID NO: 7), G-D-G-G (SEQ ID NO: 8), D-G-G-L (SEQ ID NO: 9) and G-G-L-F (SEQ ID NO: 10) for the manufacture of a medicament for the treatment and/or prevention of a neurodegenerative disease.

According to the present invention all peptides disclosed herein and exhibiting neurotrophic and/or neurogenic activity may be used for manufacturing a medicament for the treatment and/or prevention of neurodegenerative diseases.

According to a preferred embodiment of the present invention the peptide is a peptide according to the present invention as defined above.

The neurodegenerative disease is preferably selected from the group consisting of Alexander disease, Alper's disease, Alzheimer disease, Amyotrophic lateral sclerosis, Ataxia telangiectasia, Canavan disease, Cockayne syndrome, Corticobasal degeneration, Creutzfeldt-Jakob disease, epilepsy, Huntington disease, Kennedy's disease, Krabbe disease, Lewy body dementia, Machado-Joseph disease (Spinocerebellar ataxia type 3), Multiple sclerosis, Multiple System Atrophy, Parkinson disease, Pelizaeus-Merzbacher Disease, Pick's disease, Primary lateral sclerosis, Refsum's disease, Sandhoff disease, Schilder's disease, Spinocerebellar ataxia, Steele-Richardson-Olszewski disease, stroke, depression and Tabes dorsalis.

Next to these preferred neurodegenerative diseases the peptide according to the present invention may also be used to treat other cerebral disorders.

In one embodiment of the invention a peptide or protein comprising or consisting of a peptide of the present invention can be employed as a drug stimulating cerebral reparative process and used for the treatment and prevention of trauma-associated cerebral lesions, including the treatment of cerebral lesions after a fracture of the cranial vault, skull base, multiple bone fractures, the treatment for the cerebral lesions in cases of intracranial trauma (e.g. posttraumatic cerebral concussion, cerebral wounds and contusion, subarachnoid, subdural and extradural haemorrhage), the treatment and prevention of traumatic shock, the treatment of the cerebral lesions associated with the impact of radiation, lowered temperature, heat and light, air pressure, electric and ultrahigh frequency current, the treatment and prevention of delayed-onset effects of skull fractures, the treatment and prevention of delayed-onset effects of intracranial trauma, the treatment and prevention of delayed-onset cerebral lesions induced by radiation, complications after surgical and other medical interventions.

In another embodiment of the present invention the peptides according to the present invention may be used as a drug suppressing toxic effects of the neurotrophic agents, stimulating cerebral repair processes and revealing cerebroprotective activity for the treatment and prevention of cerebral lesions after poisoning including the treatment of cerebral lesions after poisoning with therapeutic agents, medicinal and biological compounds, the treatment of the cerebral impairment with agents of non-medical origin, the treatment and prevention of delayed-onset cerebral lesions induced by poisoning with drugs and non-medical substances.

In another embodiment of the present invention the peptides according to the present invention may be used as drug with nootropic activity and stimulating cerebral repair processes for the treatment and prevention of mental deficiencies.

In another embodiment of the present invention the peptides according to the present invention may be used for stimulating cerebral repair processes and motional activity for the treatment and prevention of paralytic disorders including the treatment and prevention of hemiplegia, the treatment and prevention of infantile cerebral paralysis, the treatment and prevention of other paralytic syndromes (quadriplegia, paraplegia, diplegia of upper extremities, monoplegia of lower extremities).

In another embodiment of the present invention the peptides according to the present invention may be used as drug stimulating cerebral repair processes with cerebroprotective activity for the treatment and prevention of cerebral impairments in case of chromosome anomalies including Down's syndrome.

In another embodiment of the present invention the peptides according to the present invention may be used as drug stimulating cerebral repair processes with cerebroprotective activity for the treatment and prevention of cerebral impairments in case of inflammatory cerebral disorders including the treatment and prevention of cerebral impairments in case of bacterial meningitis including cryptococcus meningitis in AIDS patients, the treatment and prevention of cerebral impairments in case of non-bacterial meningitis, the treatment and prevention of cerebral impairments in case of meningitis of unclear origin, the treatment and prevention of cerebral impairments in case of encephalitis, myelitis and encephalomyelitis, including cerebral toxoplasmosis in AIDS patients, for the treatment and prevention of cerebral impairments in case of intracranial abscesses, for the treatment and prevention of cerebral impairments in case of phlebitis and thrombophlebitis of intracranial venous sinus, for the treatment and prevention of sequalae after intracranial abscesses or purulent infection.

In another embodiment of the present invention the peptides according to the present invention may be used as drug stimulating cerebral repair processes with cerebroprotective and nootropic activity for the treatment and prevention of cerebral impairments in case of cerebral-vascular disorders including the treatment and prevention of cerebral impairments in case of subarachnoid haemorrhage, treatment and prevention of cerebral impairments in case of cerebral haemorrhage, the treatment and prevention of cerebral impairments in case of occlusion and Stenosis of precerebral arteries, the treatment and prevention of cerebral impairments in case of occlusion of cerebral arteries, the treatment and prevention of cerebral impairments in case of transitory cerebral ischemia, the treatment and prevention of cerebral impairments in case of other cerebral-vascular disorders (acute cerebral-vascular disorders, cerebral atherosclerosis and other generalised cerebral-vascular disorders, hypertension encephalopathy, cerebral aneurysm, cerebral arteritis and non-purulent thrombosis of intracranial venous sinus).

In another embodiment of the present invention the peptides according to the present invention may be used as drug stimulating cerebral repair processes, having cerebroprotective and nootropic activity for the treatment and prevention of alcoholic psychosis including the treatment and prevention of delirium tremens at abstinence syndrome, the treatment and prevention of alcoholic amnestic syndrome and other alcoholic dementia disorders, the treatment and prevention of pathologic alcoholic intoxication, the treatment and prevention of alcoholic paranoia and alcoholic psychosis of paranoid type.

In another embodiment of the present invention the peptides according to the present invention may be used as drug stimulating cerebral repair processes, having cerebroprotective and nootropic activity for the treatment and prevention of cerebral impairment in case of alcoholism.

In another embodiment of the present invention the peptides according to the present invention may be used as a drug suppressing toxic effects of neurotropic agents and having cerebroprotective and nootropic activity for the treatment and prevention of drug-induced psychosis including the treatment and prevention of the drug abstinence syndrome, the treatment and prevention of drug-induced paranoid and/or hallucinatory disorders, the treatment and prevention of pathologic intoxication with medical agents, the treatment and prevention of other drug-induced psychic disorders (delirium, dementia, amnestic syndrome and organic affective syndrome).

In another embodiment of the present invention the peptides according to the present invention may be used as a drug suppressing toxic effects of neurotropic agents and having cerebroprotective activity for the treatment and prevention of drug addiction including the treatment and prevention of addiction to opioid agents, the treatment and prevention of addiction to barbiturate, sedative agents and tranquillisers, the treatment and prevention of cocaine addiction, the treatment and prevention of addiction to cannabis and derivatives thereof, the treatment and prevention of addiction to amphetamine and psychostimulating agents, the treatment and prevention of addiction to hallucinogenic agents, treatment and prevention of cerebral impairments caused by drug abuse without drug addiction (abuse of alcohol, tobacco, cannabis, hallucinogens, opioids, cocaine, psychostimulating agents, antidepressants).

In another embodiment of the present invention the peptides according to the present invention may be used as an agent for treatment and prevention of psychogenic symptoms and syndromes including the treatment and prevention of psychogenic physiologic impairments, the treatment and prevention of other psychogenic symptoms and syndromes (stammering and impediments, psychogenic anorexia tics, repeated stereotype movements, inorganic sleep disorders, psychogenic diet disorders, enuresis, psychalgia), the treatment and prevention of acute stress response, the treatment and prevention of reactions induced by psychological directions.

In another embodiment of the present invention the peptides according to the present invention may be used as an agent for treatment and prevention of inorganic psychoses including the treatment and prevention of Schizophrenie disorders, the treatment and prevention of affective psychoses, the treatment and prevention of paranoid conditions, the treatment and prevention of other inorganic psychoses (psychoses of depressive and agitate types, reactive confusion, acute paranoid reactions, psychogenic paranoid psychoses) and non-differentiated psychoses including psychoses induced with cerebral impairments in AIDS patients, the treatment and prevention of infantile psychoses including infantile autism and disintegrative psychoses.

In another embodiment of the present invention the peptides according to the present invention may be used as a drug stimulating cerebral repair processes and having cerebroprotective and nootropic activity for the treatment and prevention of cerebral impairments in case of other cerebral disorders including the treatment and prevention of cerebral impairments in case of cerebral cysts, the treatment and prevention of hypoxic cerebral damage, the treatment and prevention of cerebral impairments in case of intracranial hypertension, the treatment and prevention of cerebral impairments in case of encephalopathy.

In another embodiment of the present invention the peptides according to the present invention may be used as drug stimulating cerebral repair processes and motional activity, having cerebroprotective and nootropic effects for treatment and prevention of symptoms and syndromes in case of various cerebral disorders including the treatment and prevention of cognitive disorders, memory and artention, impairments (for instance, in case of amnestic diseases, mental deficiency, inorganic psychoses, etc.), the treatment and prevention of aphasia and apraxia (for instance, in case of amnestic diseases, inorganic psychoses, cerebral impairments due to chromosome anomalies, etc.), the treatment and prevention of emotional disorders (for instance, in case of inorganic psychoses, demyelinising cerebral disorders, etc.), the treatment and prevention of psychopathologic syndrome (for instance, in case of transitional organic psychotic conditions, drug-induced psychoses, drug addiction, etc.), the treatment and prevention of asthenic-depressive syndrome (for instance, in case of inorganic psychoses, cerebral impairments due to chromosome anomalies, etc.), the treatment and prevention of delirium syndrome (for instance, in case of drug-induced psychoses and drug addiction, inorganic psychoses, etc.), the treatment and prevention of sleep disorders (for instance, in case of cerebral tumours, transitional organic psychotic conditions, etc.), for treatment and prevention of cerebral-focal syndrome (focal pathologic symptoms) (for instance, in case of cerebral impairments caused by complications of surgical or other medical intervention, demyelinising cerebral disorders, etc.), the treatment and prevention of syndrome of motor disorders (for instance, in case of cerebral tumours, cerebral impairments caused by poisoning, etc.), the treatment and prevention of peripheral neuropathy, preferably diabetic neuropathy.

According to a preferred embodiment of the present invention the medicament further comprises a pharmaceutical acceptable excipient and/or carrier as defined above.

According to another preferred embodiment of the present invention the composition further comprises at least one additional pharmaceutically active component.

The medicament is preferably provided for intravenous, intramuscular, spinal, epidural, transdermal, subcutaneous, intranasal, mucosal, parenteral, oral, enteral or rectal administration.

According to a preferred embodiment of the present invention the medicament comprises the peptide in an amount between 0.1 µg/g to 100 mg/g, preferably 1 µg/g to 80 mg/g.

It is in particular preferred to use as peptide in a medicament of the present invention a peptide having the amino acid sequence SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9 and/or SEQ ID NO: 10.

Another aspect of the present invention relates to a method for preventing a break out of a neurodegenerative disease in an individual and for treating an individual suffering from a neurodegenerative disease comprising the administration of a pharmaceutical composition or of an effective amount of at least one peptide according to the present invention.

The term "effective amount" of a peptide as used herein will depend among other factors on the route of administration and physical condition of the individual to be exposed to said peptide. Methods for the determination of the effective amount are known to the skilled person.

The neurodegenerative disease is preferably selected from the group consisting of Alexander disease, Alper's disease, Alzheimer disease, Amyotrophic lateral sclerosis, Ataxia telangiectasia, Canavan disease, Cockayne syndrome, Corticobasal degeneration, Creutzfeldt-Jakob disease, epilepsy, Huntington disease, Kennedy's disease, Krabbe disease, Lewy body dementia, Machado-Joseph disease (Spinocerebellar ataxia type 3), Multiple sclerosis, Multiple System Atrophy, Parkinson disease, Pelizaeus-Merzbacher Disease, Pick's disease, Primary lateral sclerosis, Refsum's disease, Sandhoff disease, Schilder's disease, Spinocerebellar ataxia, Steele-Richardson-Olszewski disease, peripheral neuropathy, diabetic neuropathy, stroke, depression and Tabes dorsalis.

According to a preferred embodiment of the present invention the peptide is administered to said individual at a dose of 0.1 µg/kg to 20 mg/kg body weight, preferably 0.5 µg/kg to 10 mg/kg body weight.

Another aspect of the present invention relates to the use of at least one peptide with neurotrophic and/or neurogenic activity and/or at least one peptide having an amino acid sequence selected from the group consisting of G-D-G-G-L-F-E-K (SEQ ID NO: 5), G-L-F-E-K-K-L-W (SEQ ID NO: 6), V-G-D-G (SEQ ID NO: 7), G-D-G-G (SEQ ID NO: 8), D-G-G-L (SEQ ID NO: 9) and G-G-L-F (SEQ ID NO: 10) for the manufacture of a medicament for improving learning memory capacities in an individual.

Another aspect of the present invention relates to the use of a molecule consisting of a maximum of 50 amino acids with neurotrophic and/or neurogenic activity comprising at least one peptide according to the present invention or IPR-NEADGMPINV (SEQ ID NO: 4) or a fragment thereof for the manufacture of a medicament for the treatment or enhancement of motor deficiencies in an individual.

The present invention is further illustrated by the following figures and examples, however, without being restricted thereto.

Figure 7:
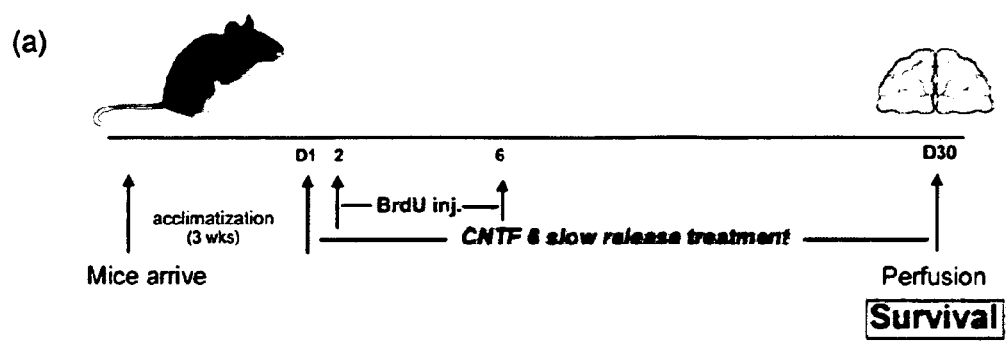
Figure 7:
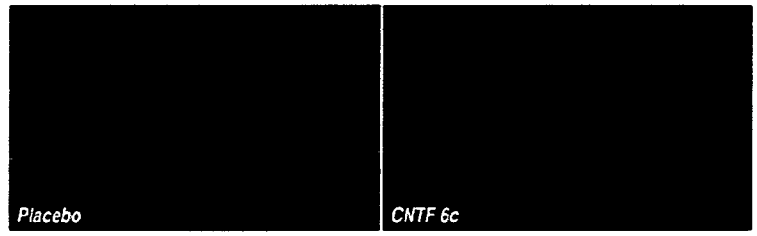
Figure 7:
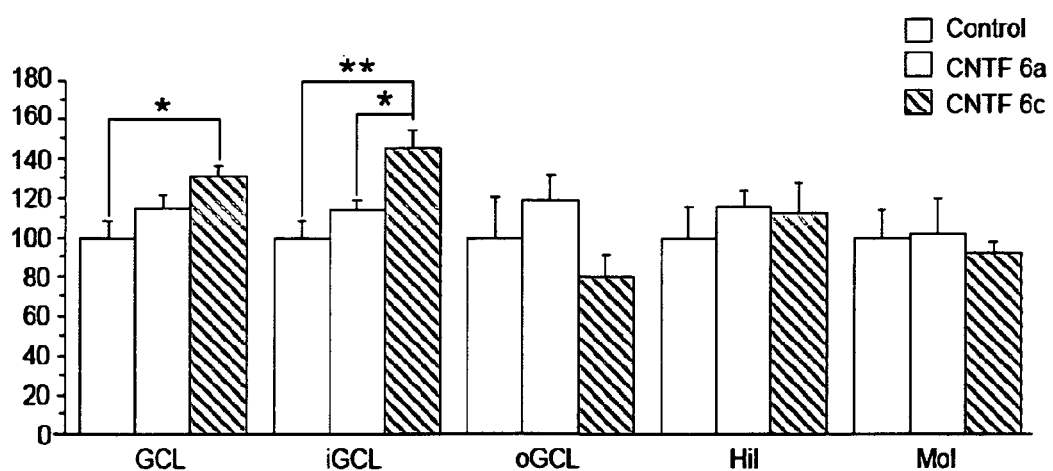

FIG. 7 (a) shows the experimental design of example 4; (b) and (c) show the proliferation of progenitors in four sub-regions of the hippocampus (for anatomical definitions, see "Materials and Methods" section): iGCL (inner granule cell layer, which included the SGZ), oGCL (outer granule cell layer), Mol (molecular layer) and Hil (hilus), revealed that compared to control group, CNTF 6c increased the number of BrdU-IR cells in the iGCL by 45% (p<0.001, Student's t-test), whereas no significant differences were observed in either oGCL, Mol or Hil.

Figure 8:
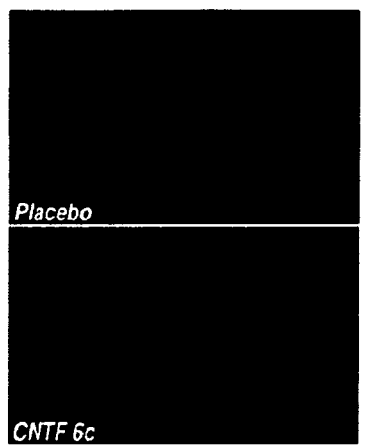
Figure 8:
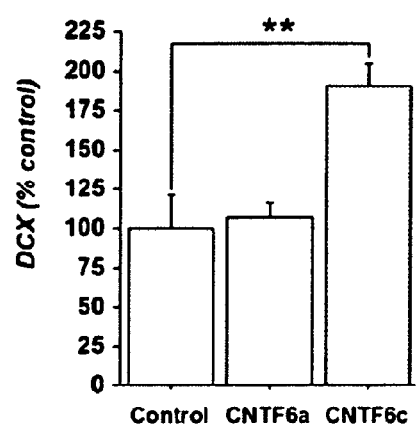
Figure 8:
Figure 8:
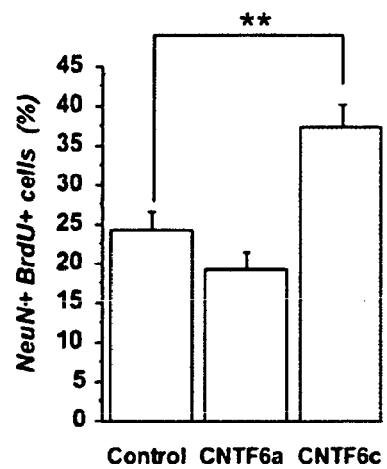

FIG. 8 shows the proliferation of immature neurons in the dentate gyrus (a) and the neuronal differentiation of progenitor cells in the dentate gyrus (b).

Figure 9:
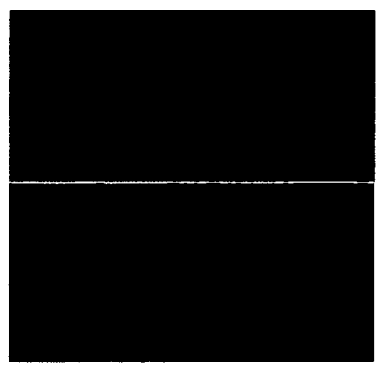
Figure 9:
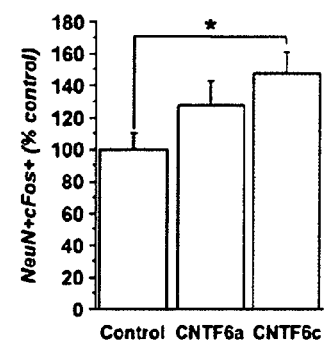
Figure 9:
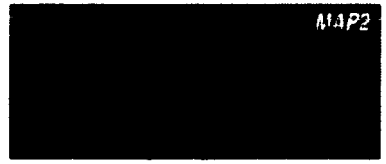
Figure 9:
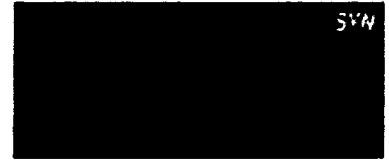
Figure 9:
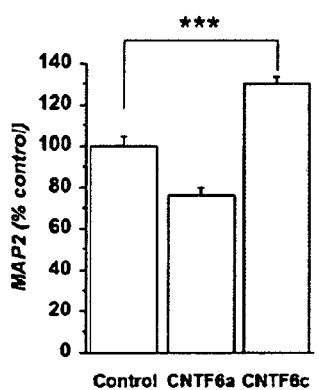
Figure 9:
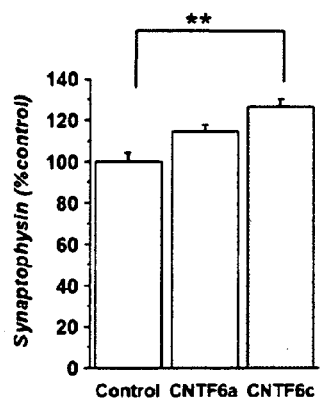

FIG. 9 shows the induction of immediate-early gene expression in resident neurons (a) and neurotrophy and neuroprotection in the dentate gyrus.

Figure 10:
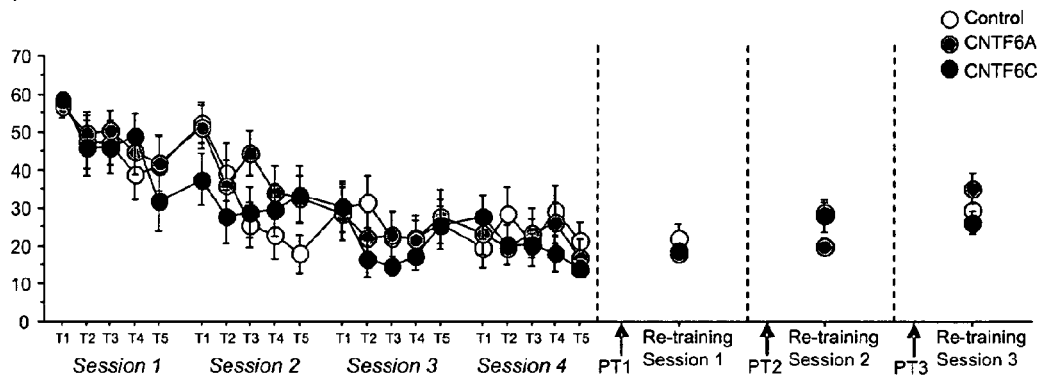
Figure 10:
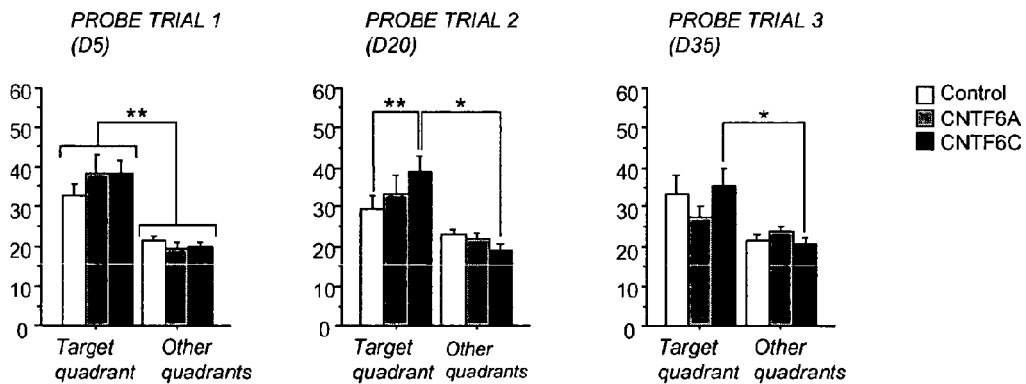
Figure 10:
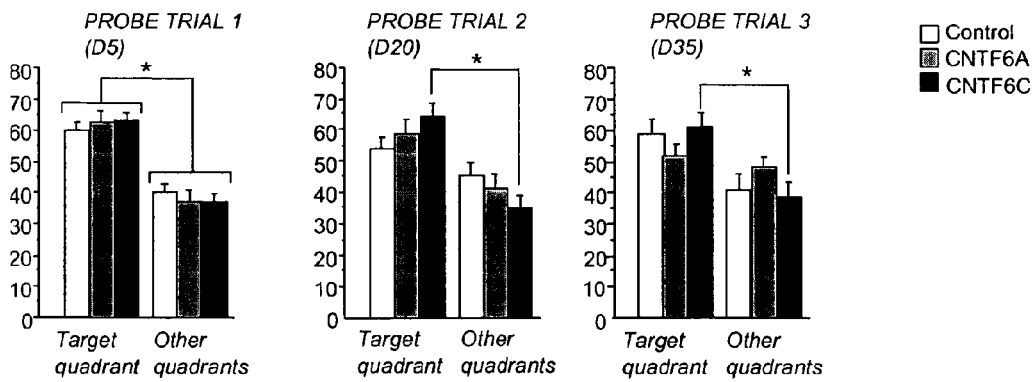

FIG. 10 shows the enhancement of memory by the administration of CNTF 6a and c.

EXAMPLES

Example 1

Dentate Gyrus Neurogenesis and Neurotrophic Activities of Peptides Derived from CNTF in Normal Adult Mice Materials:

All experiments involving mice were done on 8-10 month old female retired breeders of C57BL6 background. A total of 33 mice were divided into 10 groups of 3 animals each (except control group which had 6 mice). The groups are described in Table 1. Details of CNTF peptides are described in Table 2.

TABLE 1

| Group | Description | Concentration | # of mice |
| --- | --- | --- | --- |
| 1 | Control [normal saline] | — | 6 |
| 2 | Peptide Mix | 0.5 nmol | 3 |
| 3 | Peptide 5-1 | 0.5 nmol | 3 |
| 4 | Peptide 5-2 | 5 nmol | 3 |
| 5 | Peptide 6-1 | 0.5 nmol | 3 |
| 6 | Peptide 6-2 | 5 nmol | 3 |

TABLE 1-continued

| Group | Description | Concentration | # of mice |
| --- | --- | --- | --- |
| 7 | Peptide 9-1 | 0.5 nmol | 3 |
| 8 | Peptide 9-2 | 5 nmol | 3 |
| 9 | Peptide 10-1 | 0.5 nmol | 3 |
| 10 | Peptide 10-2 | 5 nmol | 3 |

TABLE 2

| CNTF Peptide | Position in CNTF | MW | SEQ ID NO: |
| --- | --- | --- | --- |
| Peptide 5 | 133-145 | 1384 | 4 |
| Peptide 6 | 145-155 | 1203 | 1 |
| Peptide 9 | 91-102 | 1427 | 2 |
| Peptide 10 | Loop | 1192 | 11 (CHQGCGGLFEC) |

Experimental Design (FIG. 1):

The animals were kept in groups of 3 per cage. The mice were given daily intraperitoneal injections of four CNTF peptides either separately or in a mixture for 2 weeks as described in Table 1. From day 2, BrdU (Bromodeoxyuridine; 150 mg/Kg) was added to the injections. The animals were sacrificed 24 hours after the last injection. Briefly, the animals were perfused transcardially with PBS and their brains taken out and dissected into halves. One hemisphere from each animal was frozen for biochemical analysis and the other was fixed in 4% paraformaldehyde for 48 hours followed by equilibration in 30% sucrose in PBS overnight. These were then processed for immunohistochemistry.

Fixed tissues were cut into 40 μm sections on a freezing sliding microtome. One in 5 sections per brain was processed for BrdU staining and visualized by immunoflorescence. Cell counting was done on these sections to determine the number of BrdU labeled cells (representing newly born cells) in the dentate gyrus of the hippocampus. The area of counting was limited to the granule cell layer and the subgranular zone (a two-nucleus thick layer adjacent to the granule cell layer). For counting purposes, the dentate gyrus was divided into two areas, the outer granule cell layer (OGCL) consisting of one half of the granule cell layer, and the subgranular zone (SGZ) of the inner half (towards the hilus) of the granule cell layer plus a two-nucleus thick layer adjacent to the outer border of the hilus. Cell counting was done on confocal images of the sections according to the optical dissector principle. Volumetric analysis was carried out with the help of Image Pro software.

Figure 2:
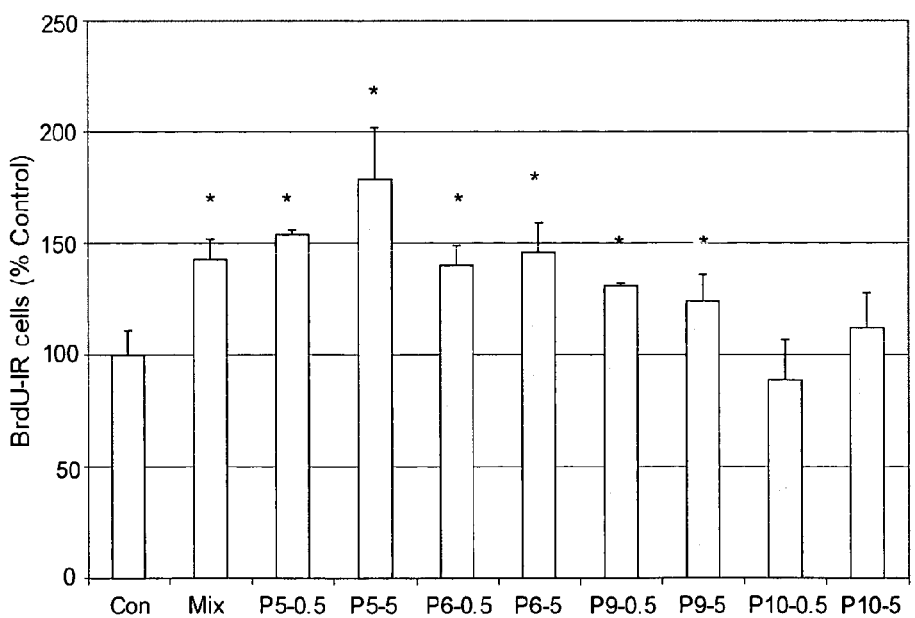
FIG. 2 shows the proliferation of dentate gyrus progenitor cells in the presence of peptides 5, 6, 9 and 10 (control).

Results:

The analysis of cell proliferation in the dentate gyrus of mice treated with individual peptides is as follows:

1.) Peptides 5, 6 and 9 induced statistically significant increase in the proliferation of dentate gyrus progenitor cells. Peptides 5 and 6 induced more proliferation than peptide 9, whereas Peptide 10 had no effect on cell proliferation (FIG. 2).

Figure 3:
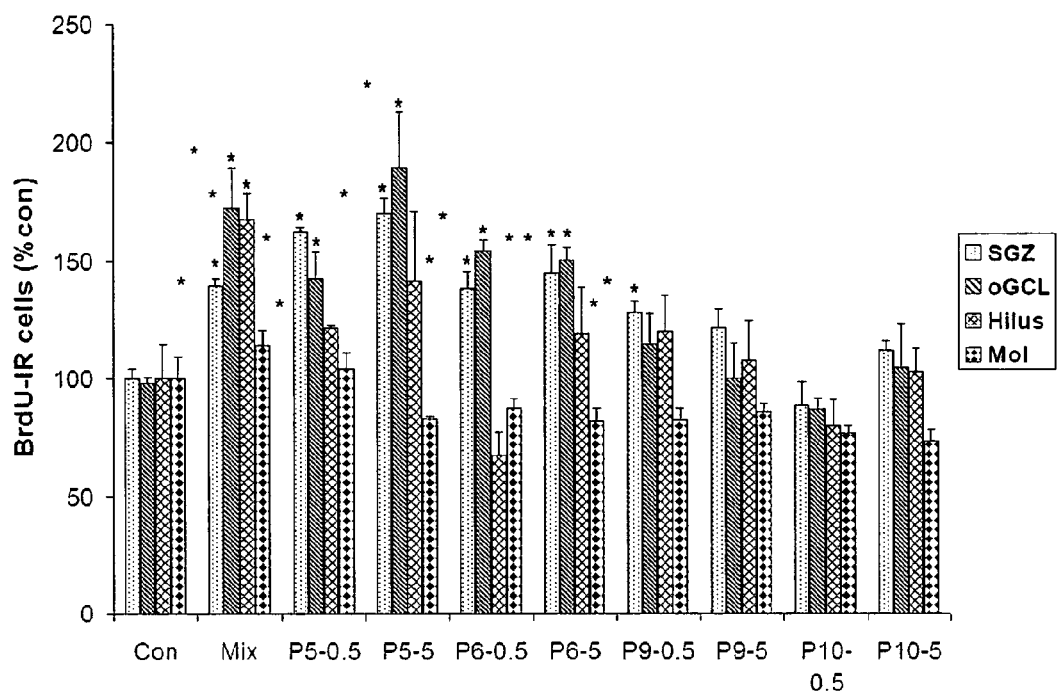
FIG. 3 shows the analysis of cell proliferation across the 3 layers of the dentate gyrus.

2.) Analysis of cell proliferation across the 3 layers of the dentate gyrus showed (FIG. 3):

a.) Peptides 5 and 6 at both concentrations (0.5 and 5 nmoles/animal) increased cell proliferation in the SGZ (subgranular zone) and OGCL (outer portion of the granule cell layer) of the dentate gyrus indicating their effect on both proliferation and migration of progenitors.

b.) Peptide 9 at 0.5 nmoles/animal increased cell proliferation in the SGZ with a similar trend at higher concentration of the peptide (5 nmoles/animal).

c.) None of the peptides alone had any effect on the number of progenitors in the hilus.

Figure 4:
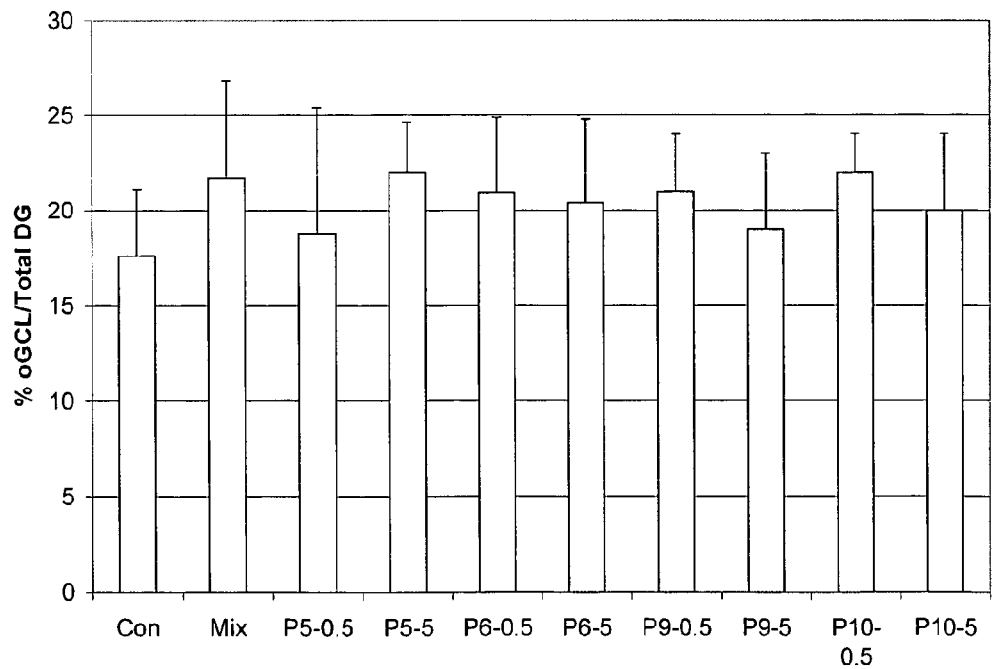
FIG. 4 shows newly born cells in oGCL.

3.) There was no evidence of ectopic cell birth in the dentate gyrus as evidenced by lack of selective increase in the percentage of newly born cells in OGCL (FIG. 4).

Example 2

Studies with Cell Based Assay

Cell-Based Assay for Differentiation

βIII-tubulin antigenicity is compromised by fixation, although longer fixation improves attachment to the plates.

Therefore, plates with different coatings for their suitability to be used in differentiation assay using CNTF (0.1, 1, 10, 100 ng/ml) were tested.

Coating Matrices Tested:
poly D-lysine
poly D-lysine/laminin
poly L-ornithine/laminin
polyethyleneimine
collagen I
fibronectin Results:

AHPs did neither divide nor differentiate on collagen I or fibronectin.

The best immunostaining for βIII-tubulin was with 10 min fixation. However, since less cells were lost with 1 hr fixation, the differentiation assay with CNTF was performed with 1 hr fixation.

The best differentiation was achieved on polyethyleneimine coated plates using the ratio of βIII-tubulin immunostaining to DAPI nuclear staining (cell number) as % of control as a relative measure of differentiation.

| Coating | βIII-tu/DAPI (% of Control) (100 ng/ml CNTF) |
| --- | --- |
| poly D-lysine | 175 |
| poly D-lysine/laminin | 240 |
| poly L-ornithine/laminin | 330 |
| poly ethyleneimine | 480 |

CNTF Peptides

| 6. | V-G-D-G-G-L-F-E-K-K-L | (SEQ ID NO: 1) |
| 2. | G-D-G-G-L-F-E-K | (SEQ ID NO: 5) |
| 3. | G-L-F-E-K-K-L-W | (SEQ ID NO: 6) |
| 6A. | V-G-D-G | (SEQ ID NO: 7) |
| 6B. | G-D-G-G | (SEQ ID NO: 8) |
| 6C. | D-G-G-L | (SEQ ID NO: 9) |
| 6D. | G-G-L-F | (SEQ ID NO: 10) |

Example 3

In example 1 it was shown that the CNTF peptides mix and Peptides 5, 6 and 9 individually induced statistically significant increase in the proliferation of dentate gyrus progenitor cells. Peptides 5 and 6 induced more proliferation than Peptide 9, whereas Peptide 10 had no effect on cell proliferation. In this example the analysis on cell proliferation and neurotrophy if further evidenced.

Figure 5:
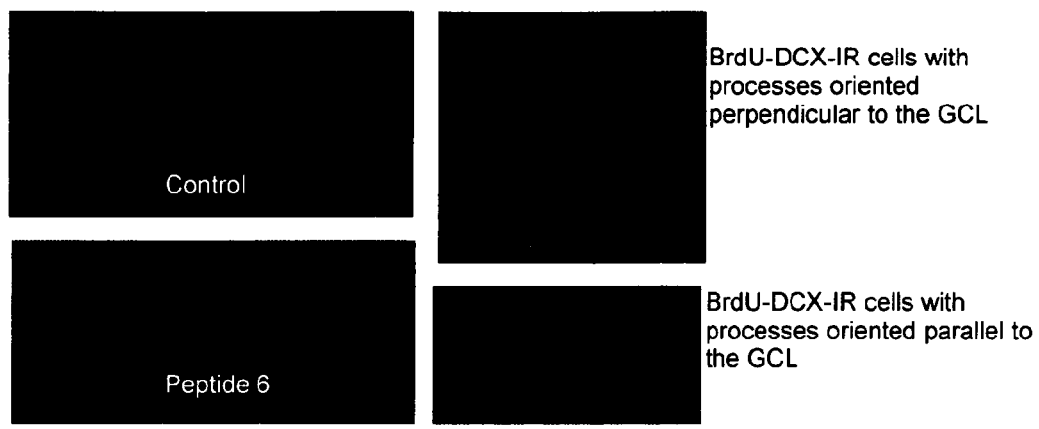
FIG. 5 shows the effect of Peptides 5, 9 and 10 on the expression of DCX in BrdU labeled progenitors in the dentate gyrus.
Figure 5:
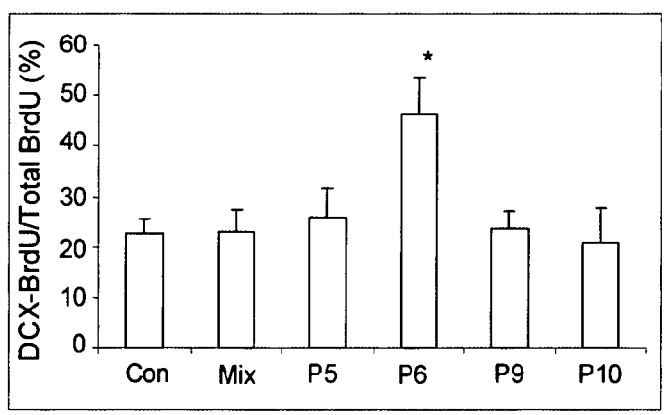

Results:

Peptide 6 induced a two fold increase in the differentiation of dentate gyrus progenitors into DCX (doublecortin) expressing cells in the 14 day treatment group. Peptides 5, 9 and 10 did not have any effect on the expression of DCX in BrdU labeled progenitors in the dentate gyrus (FIG. 5).

Figure 6:
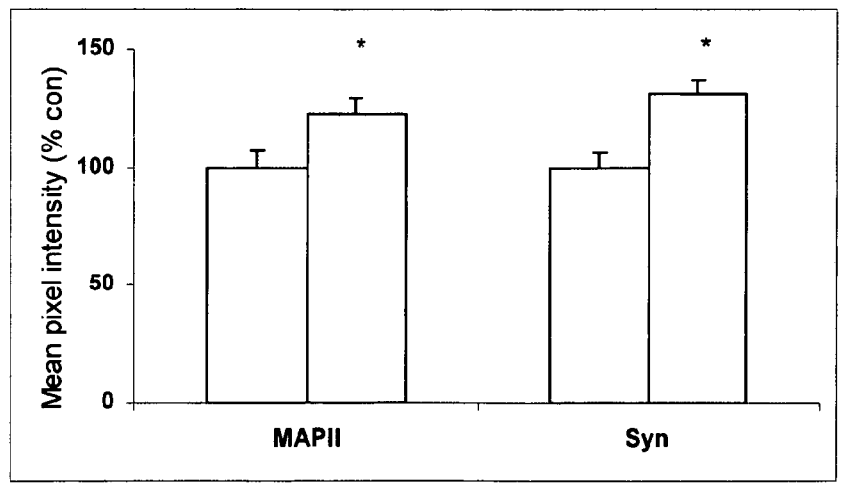
FIG. 6 shows the MAP2 and synaptophysin immunoreactivity in the dentate gyrus when Peptide 6 is administered.

Peptide 6 caused a statistically significant increase in MAP2 and synaptophysin immunoreactivity in the dentate gyrus of treated mice as measured by mean pixel intensity in the outlined area of interest (FIG. 6).

Behavioral tests employing Morris Water maze task-based memory acquisition, retention and recall paradigms have also been carried out. Two groups of 18 mice each were treated with Peptide 6/Placebo containing implantable subcutaneous pellets with user specified timed release kinetics: 14 days for group 1 and 30 days for group 2. In particular, the 30 day group showed significant improvement in memory acquisition as evaluated by time spent in the target quadrant and distance covered in the target quadrant in the Morris Water Maze task.

Materials & Methods:

All experiments involving mice were done on 8-10 month old female retired breeders of C57BL6 background. A total of 33 mice were divided into 10 groups of 3 animals each (except control group which had 6 mice). The groups are described in Table 1. Details of CNTF peptides are described in Table 2.

Figure 1:
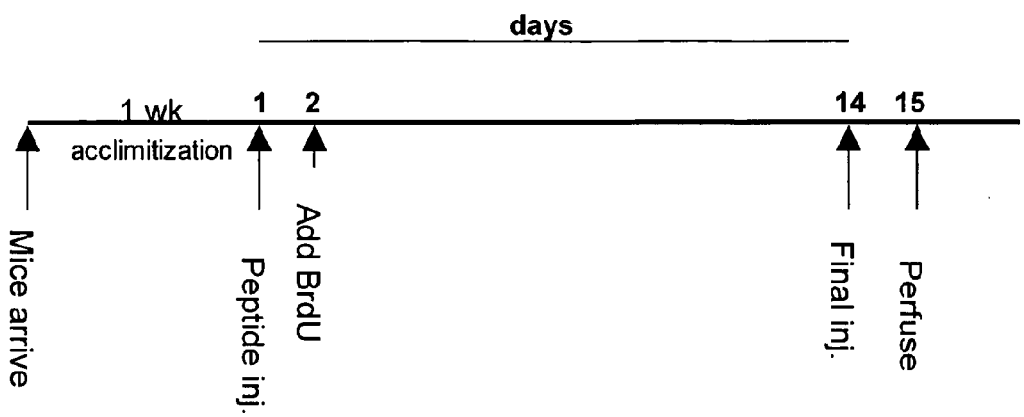
FIG. 1 shows the experimental design.

The animals were kept in groups of 3 per cage. The mice were given daily intraperitoneal injections of four CNTF peptides either separately or in a mixture for 2 weeks as described in table 1. From day 2, BrdU (Bromodeoxyuridine; 150 mg/Kg) was added to the injections. The animals were sacrificed 24 hours after the last injection (FIG. 1). Briefly, the animals were perfused transcardially with PBS and their brains taken out and dissected into halves. One hemisphere from each animal was frozen for biochemical analysis and the other was fixed in 4% paraformaldehyde for 48 hours followed by equilibration in 30% sucrose in PBS overnight. These were then processed for immunohistochemistry.

Fixed tissues were cut into 40 μm sections on a freezing sliding microtome. One in 5 sections per brain was processed for BrdU staining and visualized by immunoflorescence. Cell counting was done on these sections to determine the number of BrdU labeled cells (representing newly born cells) in the dentate gyrus of the hippocampus. The area of counting was limited to the granule cell layer and the subgranular zone (a two-nucleus thick layer adjacent to the granule cell layer). For counting purposes, the dentate gyrus was divided into two areas, the outer granule cell layer (OGCL) consisting of out half of the granule cell layer, and the subventricular zone (SVZ) comprising of the inner half (towards the hilus) of the granule cell layer plus a two-nucleus thick layer adjacent to the outer border of the hilus. Cell counting was done on confocal images of the sections according to the optical dissector principle. Volumetric analysis was carried out with the help of Image Pro software.

Example 4

Enhancement of Adult Hippocampal Neurogenesis and Spatial Memory by a CNTF-Based Tetrapeptide Materials and Methods
Animals and Housing:

All in vivo studies for characterization of peptides (stereology and behavioral analysis) were performed on 8-10-month-old female retired breeders of C57B16 background. The animals were acclimatized for at least 3 weeks to exclude occasional pregnant mice from the studies. Mice were group-housed (3 animals per cage) with a 12:12 light:dark cycle and with free access to food and water. All procedures were conducted in accordance with approved protocols from our institutional Animal Welfare Committee.

Construction of CNTF-Based Tetrapeptides:

In the preceding examples an 11-mer peptide based on epitope mapping of neutralizing antibodies to human CNTF with significant neurogenic and neurotrophic activity in the adult mouse dentate gyrus has been identified. Based on this peptide, CNTF 6, a set of four tetrapeptides with overlapping residues to the sequence of the parent peptide CNTF 6 (see Table 3) was further constructed. These peptides, CNTF 6a-d, were synthesized on a commercial basis by the Pan Biotechnology Facility of Stanford University (Palo Alto, Calif.).

TABLE 3

| CNTF Peptide | Position in CNTF |
|---|---|
| Peptide 6a | 145-148 |
| Peptide 6b | 146-149 |
| Peptide 6c | 147-150 |
| Peptide 6d | 148-151 |

Treatment of Animals with Peptides:

To study neurogenesis, mice received subcutaneous implants of extended release depot pellets containing either CNTF peptides 6a or 6c for 30 days of continuous dosing (Innovative Research of America, Sarasota, Fla.). For control groups, the pellets consisted of the carrier biopolymer only. For implantation, the mice were anesthetized with 2.5% Avertin (0.38 ml for a 25 g animal). Under sterile conditions, the pellets were then subcutaneously implanted along the anterolateral aspect of the right shoulder with a precision trochar (Innovative Research of America). The animals were then transferred to the animal colony after recovery from anesthesia. There were no complications associated with the implantation and treatment. BrdU was given as two daily i.p. injections (100 mg/kg/dose) for five days starting on day 2 of peptide treatment. Neurogenesis was assessed in the dentate gyrus (DG) by counting the number of BrdU-immunoreactive (BrdU-IR), BrdU-DCX-IR and BrdU-NeuN-IR cells in various layers of the DG. Employing principles of unbiased stereology, the optical fractionator method was used to estimate cell counts for the DG.

Antibodies:

The following primary antibodies were used for immunohistochemistry:anti-BrdU (1:400; Accurate) a rat monoclonal raised against BrdU; anti-DCX (1:200; Santa Cruz Biotechnology Inc.), a goat polyclonal antibody raised against an 18-amino acid peptide representing residues 384-410 of human doublecortin; anti-NeuN (1:500; Chemicon), a mouse monoclonal antibody raised against purified cell nuclei from mouse brain; Anti-c-Fos (Ab-5) (1:500; Calbiochem), a rabbit polyclonal antibody raised against a synthetic peptide corresponding to amino-acids 4-17 of human c-Fos; SMI52 (1:1000; Sternberger Monoclonals), a mouse monoclonal antibody specific for the mature neuronal marker MAP2a,b; anti-synaptophysin, SYN (1:200; Chemicon), a mouse monoclonal anti-body raised against vesicular fraction of bovine brain. The following secondary antibodies were used: Alexa 488-conjugated goat anti-mouse IgG antibody and Alexa 594-conjugated goat anti-rabbit or anti-rat IgG antibody (Molecular Probes); biotinylated anti-rat IgG antibody and Cy5-conjugated goat anti-mouse anti-body (Jackson ImmunoResearch).

Tissue Processing:

At the end of treatment, all animals were anesthetized with an overdose of sodium pentobarbital and transcardially perfused with 0.1 M PBS. After perfusion, the brains were removed from the skull, the left hemisphere was immediately frozen for future biochemical analysis and the right hemisphere was fixed in 4% paraformaldehyde in 0.1 M PBS for at least 24 hours at room temperature. Tissues were then stored in 30% sucrose solutions at 4° C. until sectioning. The brains were sectioned sagittaly on a freezing sliding microtome at 40 μm through the entire hippocampus and the sections were stored in glycol anti-freeze solution (Ethylene glycol, glycerol and 0.1 M PBS in 3:3:4 ratio) at −20° C. till further processing.

Immunohistochemistry:

Immunohistochemistry was performed as described elsewhere (Kuhn et al., J. Neurosci 17 (15) (1997): 5820-5829). Briefly, every $5^{th}$ brain section was chosen for quantification of cell number and every $10^{th}$ section was chosen for staining intensity scanning. Immunohistochemistry was performed on free floating sections. For BrdU immunohistochemistry, epitope retrieval and staining were performed as previously described (Kuhn et al., J. Neurosci 17 (15) (1997): 5820-5829).

Definitions, Stereology and Confocal Imaging:

Neurogenesis was assessed in the DG by counting the number of BrdU-immunoreactive (BrdU-IR), BrdU-DCX-IR and BrdU-NeuN-IR cells in various layers of the DG. The granule cell layer (GCL) was subdivided into an inner and outer half (iGCL and OGCL). The iGCL consisted of the subgranular zone (SGZ, defined as a 2-3 nuclei thick layer bordering the GCL) and the inner half of the GCL adjacent to the Hilus (Hil); the outer GCL (OGCL) was defined as the half of the GCL adjacent to the Molecular layer (Mol). A cell in the middle of the GCL was considered part of the iGCL and a cell bordering the GCL in the Mol was included in oGCL counts. Mol was defined as the region between the superior limb of GCL and hippocampal fissure and between the inferior limb of the GCL and the inferior borders of the DG. Hil included the superficial polymorphic layer.

All sections were collected using the random uniform sampling scheme. For BrdU-IR cells, counting was performed on every $5^{th}$ section using 40× oil objective of a Nikon 90i fluorescent microscope equipped with Nikon C1 three laser confocal system and a Nikon DS U1 digital camera. Employing principles of unbiased stereology, the optical fractionator method was used to estimate cell counts for the DG (West et al., Anat Rec 231 (1991): 482-497). All layers of the DG described above were analyzed separately for cell counting. For each brain, at least 100 cells were counted based on coefficient of error determinations.

For BrdU-DCX-, BrdU-NeuN-, and c-Fos-NeuN-IR cells, only GCL (consisting of iGCL and oGCL described above) was counted using 100× oil objective in every $10^{th}$ section. To ensure objectivity, z-stacks were collected for each double IR cell and analyzed later by generating maximum projection and 3D constructs. A cell was counted only when it showed double IR on 3D reconstructed images.

For MAP2 and Synaptophysin IR, the entire area of GCL was outlined on every $10^{th}$ section. Maximum projection images were then generated based on confocal z-stacks, and the antibody staining was quantitated by measuring mean pixel intensity (MPI) with the help of Image-Pro Plus 5.0 software (Media Cybernetics).

All quantitations based on immunohistochemistry were verified independently on coded slides by a second investigator.

Morris Water Maze Task:

For behavioral studies, performance on the Morris Water Maze task was assessed in three groups of 10 mice each (placebo, CNTF6a and CNTF6c) which received peptide treatment for 30 days. To avoid daily stress due to injections, all animals undergoing behavioral studies received subcutaneous implants of CNTF 6a, CNTF 6c or placebo pellets as described above.

All animals for behavioral testing were coded such that the experimenter was blind to the assignment of the animals to specific treatment groups. The Morris Water Maze procedure was performed using a 110 cm diameter circular tank. Before training, the mice were handled gently for 2-3 min/day during 3 days to minimize non-specific stress. Acquisition was started with the submerged (invisible) escape platform in the North-East quadrant and each animal was given 60 sec to find the submerged escape platform. If the mouse did not find the platform in 60 sec, it was guided to it. Five such acquisition trials were given on each day, for four consecutive days. A test for retention, or probe trial, was given 24 hours later. During the probe trial the mouse was allowed to swim in the tank without the escape platform for 60 seconds. This was followed by second and third probe trials 15 and 30 days from the first probe trial. Each probe trial was immediately followed by a "retraining session" consisting of 5 trials/animal to consolidate learned behavior.

The measures of learning were the time and distance swum to reach the escape platform. For retention during the probe trial, the tank was divided into four imaginary quadrants and a small zone where the escape platform had been (virtual platform). The measures of retention were the percent of time spent and the percent of distance swum in each quadrant, and the number of entries into the platform zone.

Mouse behavior in the Morris Water Maze was monitored by a Samsung Digital Camera (SDC 4304) mounted to the ceiling and tracked and timed by a SMART (Pan Lab/San Diego Instruments) version 2.0.14 software.

Statistics:

Data are represented as mean±SEM. For analysis involving multiple groups, ANOVA with post hoc Tukey's test was used. For analysis of data with skewed distributions, the non-parametric Mann-Whitney U-test was used. For all other comparisons (including inter-group comparisons), Student's t-test was used. Differences with $p<0.05$ were considered significant.

Results:

Proliferation of Neural Progenitor Cells with Synthetic Peptides:

The four CNTF tetrapeptides were initially screened in a behavioral paradigm employing the Morris Water Maze. Two CNTF tetrapeptides, CNTF 6a and CNTF 6c, were chosen for detailed stereological and behavioral analysis.

Fifteen mice were divided into 3 groups including placebo, CNTF 6a and CNTF 6c. Mice received subcutaneous implants of 30-day extended release pellets containing either CNTF 6a or CNTF 6c (50 nmol/peptide/animal/day, n=5/group) or placebo (n=5). Dividing cells were labeled with BrdU given i.p. for five days, twice a day (100 mg/kg/animals/dose; FIG. 7a). Compared to the placebo group, CNTF 6c increased BrdU-immunoreactive (BrdU-IR) cell counts in the GCL by 31% ($p<0.05$, Student's t-test). CNTF 6a had not significant effect on cell proliferation in the GCL (FIG. 7b, c and Table 2).

Further examination of the proliferation in four sub-regions of the hippocampus (for anatomical definitions, see "Materials and Methods" section): iGCL (inner granule cell layer, which included the SGZ), oGCL (outer granule cell layer, Mol (molecular layer) and Hil (hilus), revealed that compared to control group, CNTF 6c increased the number of BrdU-IR cells in the iGCL by 45% ($p<0.001$, Student's t-test), whereas no significant differences were observed in either OGCL, Mol or Hil (FIGS. 7b and c, Table 4). CNTF 6a had no effect on BrdU-IR cell numbers in either of the four sub-regions of the DG. Together, these data suggest that both CNTF 6c increased BrdU-IR cells in the DG and this increase was mainly confided to the iGCL, the neurogenic niche of the hippocampus.

TABLE 4

Stereological counts (±SEM) of BrdU-IR cells in various subregions of the hippocampus in 30-day treated mice (n = 5/group)

|  | GCL | iGCL | oGCL | Mol | Hil |
| --- | --- | --- | --- | --- | --- |
| Control | 427 ± 38 | 334 ± 28 | 93 ± 19 | 526 ± 77 | 108 ± 17 |
| CNTF 6a | 493 ± 28 | 382 ± 15* | 110 ± 13 | 538 ± 99 | 126 ± 8 |
| CNTF 6c | 560 ± 24* | 486 ± 31** | 74 ± 10 | 487 ± 28 | 121 ± 16 |

*$p<0.05$,
**$p<0.01$, Student's t-test

Proliferation of Immature Neurons in the Dentate Gyrus:

Doublecortin (DCX), an immature neuronal marker, is used to quantitate early neuronal fate determination in DG progenitors. The number of DCX-IR cells in the GCL (iGCL+OGCL) was quantitated at the time of perfusion, a snapshot-quantitation of immature neurons in response to 30-day treatment with CNTF tetrapeptides (FIG. 8a). Stereological analysis revealed that compared to the placebo, CNTF 6c treatment increased DCX-IR cells in the GCL by almost 2 folds (~91%, increase, $p<0.001$, Student's t-test), whereas CNTF 6a treatment did not show any significant difference (FIG. 8a and Table 5). These data suggest that at the time of perfusion, there were more immature neurons in the GCL of CNTF 6c treated animals. Whether this also reflects early neuronal differentiation of dividing progenitors cannot be determined by our study.

TABLE 5

Stereological counts (±SEM) of cells expressing various neuronal maturity and/or activity markers in the granule cell layer of the dentate gyrus in 30-day treated mice (n = 5/group)

|  | DCX | NeuN-BrdU/BrdU | c-fos-NeuN |
| --- | --- | --- | --- |
| Control | 306 ± 72 | 24 ± 2 | 168 ± 17 |
| CNTF 6a | 360 ± 33 | 19 ± 2 | 214 ± 27 |
| CNTF 6c | 656 ± 43** | 39 ± 2** | 247 ± 23* |

*$p<0.05$,
**$p<0.01$, Student's t-test

Neuronal Differentiation of Progenitor Cells in the Dentate Gyrus:

Net neurogenesis in the DG is determined by the number of progenitors which survive as mature neurons, as more than half of the progenitors either die as stem cells or as immature precursors (eg. DCX-IR cells). In order to determine whether CNTF 6c induced differentiation of DG progenitors into mature neurons, the number of BrdU-IR cells expressing the mature neuronal marker NeuN in the GCL of the DG was counted. A 62% increase in BrdU-NeuN-IR cells in CNTF 6c treated animals was found when compared with the placebo group, whereas CNTF 6a treatment had no effect (p<0.01, Stundent's t-test; FIG. 8b and Table 5).

Induction of Immediate-Early Gene Expression in Resident Neurons:

For neurogenesis to have physiological significance, newly born neurons need to be functionally integrated into the hippocampal circuitry. Neuronal activity, an indication of functional integration, can be indirectly quantitated by studying changes in the expression of immediate-early genes like c-fos and zif. Towards that aim, we investigated whether CNTF 6c induced an increase in c-fos protein expression, providing a biological substrate for neuronal firing, and ultimately spatial encoding. Stereological counts of c-fos expressing mature DG neurons without behavioral stimulation, i.e. at basal levels reflecting activity in the cage (FIG. 9a and Table 5) were compared. It was found a ~47% increase in the number of mature neurons (NeuN-IR) co-expressing c-fos in the GCL in CNTF 6c treated mice (p<0.05, Student's t-test). There was also evidence of increased neuronal activity in newly born mature neurons as some BrdU-NeuN-IR cells in the GCL also co-expressed zif (FIG. 9a).

Neurotrophy and Neuroprotection in the Dentate Gyrus:

Microenvironment within the brain undergoes significant changes in both aging and disease. The rate of neurogenesis and synaptogenesis in the brain indirectly reflect its microenvironment. In order to study whether CNTF 6c-induced enhancement of DG neurogenesis was also accompanied by changes in local neurotrophy, the expression of MAP2 and synaptophysin, indicators of dendritic arborization and synaptic activity respectively, in the GCL of treated animals was measured. An increase in both indicators of neurotrophy (31% and 26% respectively, p<0.01, Student's t-test) as measured by mean-pixel intensity was found (FIG. 9b).

Enhancement of Memory:

Increased neuronal differentiation of DG progenitors, enhanced neuronal firing, upregulated synaptogenesis and neurotrophy are all key biological substrates of memory processing within the DG. Therefore, it was evaluated whether CNTF 6c treatment also had an effect on the cognitive function of treated animals. Since normal adult mice were used as experimental animals, it was crucial not to miss any effect on memory acquisition and learning that the 30-day peptide treatment might have had. Therefore, a partial training paradigm was used to evaluate learning and memory in the Morris Water Maze. Treated mice were trained on the Morris Water Maze for a total of 20 sessions spanning 4 days after which they were subjected to the first probe trial (P1). Two additional probe trials (P2 and P3) were administered 15 and 30 days after P1. Each probe trial was immediately followed by 4 retraining sessions to allow memory consolidation (FIG. 10a). Learning was evaluated in terms of latency and distance traveled to reach the invisible escape platform. Retention was measured on probe trials by the percent of time and travel distance in the target quadrant, and the number of crossings of the virtual platform.

Animals in all tree groups learned well as evident by declining swim latencies to reach the submerged platform (FIG. 10a). However, there was no effect of either CNTF 6a or CNTF 6c treatment on learning in the spatial reference memory task (two way ANOVA, p=0.667).

Analysis of retention on the three probe trials showed no effect of the treatment on P1, whereas P2 and P3 showed significant differences in both measures of retention in CNTF 6c treated mice. Analysis of time spent in the target quadrant across three probe trials indicated that whereas all animals spent equal amount of time on P1, both placebo and CNTF 6a treated animals reduced this time during subsequent P2 and P3. CNTF 6c-treated animals however, spent the same percent amount of time in the target quadrant during the three probe trials, indicating better preservation of the memory trace in these mice (FIG. 10b). Analysis of the percent distance traveled within the target quadrant also presented a similar picture for CNTF 6c across the three probe trials (FIG. 10c).

Together, these data indicate better consolidation of learned behavior due to CNTF 6c treatment.

The invention claimed is:

1. An isolated neurotrophic peptide consisting of the amino acid sequence VGDGGLFEKKL (SEQ ID NO: 1).

2. A pharmaceutical composition comprising a neurotrophic peptide consisting of the amino acid sequence GDGGLFEK (SEQ ID NO: 5), GLFEKKLW (SEQ ID NO: 6), VGDG (SEQ ID NO: 7), DGGL (SEQ ID NO: 9), or GGLF (SEQ ID NO: 10) in a pharmaceutically acceptable excipient and/or carrier.

3. The composition of claim 2, wherein the composition is suitable for intravenous, intramuscular, spinal, epidural, transdermal, subcutaneous, parenteral, intranasal, mucosal, oral, enteral, and/or rectal administration.

4. The composition of claim 2, wherein the composition is a slow release formulation.

5. The composition of claim 2, wherein the peptide is comprised in the composition in an amount between 0.1 µg/g to 100 mg/g.

6. The composition of claim 5, wherein the peptide is comprised in the composition in an amount between 1 µg to 80 mg/g.

7. A method of treating a subject comprising:
obtaining a pharmaceutical composition of claim 2; and
providing the composition to a subject;
wherein a learning-memory capacity is improved in the subject, and/or neurogenesis is promoted in the subject.

8. The method of claim 7, wherein learning-memory capacities are improved in the subject.

9. The method of claim 7, wherein the composition further comprises at least one additional pharmaceutically active component.

10. The method of claim 7, wherein the composition is provided intravenously, intramuscularly, spinally, epidurally, intranasally, mucosally, transdermally, subcutaneously, parenterally, orally, enterally, or rectally.

11. The method of claim 7, wherein the composition is a slow release formulation.

12. The method of claim 7, wherein the composition comprises the peptide in an amount between 0.1 µg/g to 100 mg/g.

13. The method of claim 12, wherein the composition comprises the peptide in an amount between preferably 1 µg to 80 mg/g.

14. The method of claim 13, wherein the peptide is administered to the subject at a dose of 0.1 µg/kg to 20 mg/kg body weight.

15. The method of claim 14, wherein the peptide is administered to the subject at a dose of 0.5 µg/kg to 10 mg/kg body weight.

16. The method of claim 7, wherein the subject is a human.

* * * * *

SEQUENCE LISTING

```
<160> NUMBER OF SEQ ID NOS: 10

<210> SEQ ID NO 1
<211> LENGTH: 11
<212> TYPE: PRT
<213> ORGANISM: Artificial
<220> FEATURE:
<223> OTHER INFORMATION: neurotrophic and/or neurogenic peptide

<400> SEQUENCE: 1

Val Gly Asp Gly Gly Leu Phe Glu Lys Lys Leu
1               5                   10

<210> SEQ ID NO 2
<211> LENGTH: 12
<212> TYPE: PRT
<213> ORGANISM: Artificial
<220> FEATURE:
<223> OTHER INFORMATION: neurotrophic and/or neurogenic peptide

<400> SEQUENCE: 2

Glu Asp Gln Gln Val His Phe Thr Pro Thr Glu Gly
1               5                   10

<210> SEQ ID NO 3
```

```
<211> LENGTH: 13
<212> TYPE: PRT
<213> ORGANISM: Artificial
<220> FEATURE:
<223> OTHER INFORMATION: neurotrophic and/or neurogenic peptide

<400> SEQUENCE: 3

Ile Pro Glu Asn Glu Ala Asp Gly Met Pro Ala Thr Val
1               5                   10

<210> SEQ ID NO 4
<211> LENGTH: 13
<212> TYPE: PRT
<213> ORGANISM: Artificial
<220> FEATURE:
<223> OTHER INFORMATION: neurotrophic and/or neurogenic peptide

<400> SEQUENCE: 4

Ile Pro Arg Asn Glu Ala Asp Gly Met Pro Ile Asn Val
1               5                   10

<210> SEQ ID NO 5
<211> LENGTH: 8
<212> TYPE: PRT
<213> ORGANISM: Artificial
<220> FEATURE:
<223> OTHER INFORMATION: neurotrophic and/or neurogenic peptide

<400> SEQUENCE: 5

Gly Asp Gly Gly Leu Phe Glu Lys
1               5

<210> SEQ ID NO 6
<211> LENGTH: 8
<212> TYPE: PRT
<213> ORGANISM: Artificial
<220> FEATURE:
<223> OTHER INFORMATION: neurotrophic and/or neurogenic peptide

<400> SEQUENCE: 6

Gly Leu Phe Glu Lys Lys Leu Trp
1               5

<210> SEQ ID NO 7
<211> LENGTH: 4
<212> TYPE: PRT
<213> ORGANISM: Artificial
<220> FEATURE:
<223> OTHER INFORMATION: neurotrophic and/or neurogenic peptide

<400> SEQUENCE: 7

Val Gly Asp Gly
1

<210> SEQ ID NO 8
<211> LENGTH: 4
<212> TYPE: PRT
<213> ORGANISM: Artificial
<220> FEATURE:
<223> OTHER INFORMATION: neurotrophic and/or neurogenic peptide

<400> SEQUENCE: 8

Gly Asp Gly Gly
1

<210> SEQ ID NO 9
<211> LENGTH: 4
<212> TYPE: PRT
```

```
<213> ORGANISM: Artificial
<220> FEATURE:
<223> OTHER INFORMATION: neurotrophic and/or neurogenic peptide

<400> SEQUENCE: 9

Asp Gly Gly Leu
1

<210> SEQ ID NO 10
<211> LENGTH: 4
<212> TYPE: PRT
<213> ORGANISM: Artificial
<220> FEATURE:
<223> OTHER INFORMATION: neurotrophic and/or neurogenic peptide

<400> SEQUENCE: 10

Gly Gly Leu Phe
1
```